United States Patent
Schulze Isfort et al.

(10) Patent No.: US 8,980,784 B2
(45) Date of Patent: Mar. 17, 2015

(54) SILICON-ALUMINUM MIXED OXIDE POWDER

(75) Inventors: Christian Schulze Isfort, Limeshain (DE); Horst-Werner Zanthoff, Muelheim a.d. Ruhr (DE); Thomas Quandt, Marl (DE); Christian Boeing, Cologne (DE)

(73) Assignee: Evonik Degussa GmbH, Essen (DE)

( * ) Notice: Subject to any disclaimer, the term of this patent is extended or adjusted under 35 U.S.C. 154(b) by 101 days.

(21) Appl. No.: 13/997,677

(22) PCT Filed: Feb. 3, 2012

(86) PCT No.: PCT/EP2012/051839
§ 371 (c)(1), (2), (4) Date: Jun. 25, 2013

(87) PCT Pub. No.: WO2012/123185
PCT Pub. Date: Sep. 20, 2012

(65) Prior Publication Data
US 2013/0303361 A1    Nov. 14, 2013

(30) Foreign Application Priority Data

Mar. 16, 2011  (EP) .................................. 11158474

(51) Int. Cl.
| | |
|---|---|
| B01J 21/12 | (2006.01) |
| C01B 33/18 | (2006.01) |
| B01J 35/00 | (2006.01) |
| B01J 35/10 | (2006.01) |
| C07C 1/20 | (2006.01) |

(52) U.S. Cl.
CPC ................ B01J 21/12 (2013.01); B01J 35/002 (2013.01); B01J 35/1014 (2013.01); B01J 35/1019 (2013.01); C01B 33/183 (2013.01); C07C 1/20 (2013.01); C01P 2002/50 (2013.01); C01P 2004/50 (2013.01); C01P 2006/12 (2013.01)
USPC ..................... 502/263; 423/327.1; 423/328.1; 423/328.2; 423/118.1; 585/640

(58) Field of Classification Search
CPC ......... B01J 21/12; C01B 33/18; C01B 33/183
USPC ............. 423/327.1, 337, 118.1, 328.1, 328.2; 502/238, 263; 585/640
See application file for complete search history.

(56) References Cited

U.S. PATENT DOCUMENTS

| | | | |
|---|---|---|---|
| 4,254,290 | A | 3/1981 | Chambers et al. |
| 7,361,714 | B2 | 4/2008 | Grass et al. |
| 7,910,786 | B2 | 3/2011 | Winterberg et al. |
| 7,919,662 | B2 | 4/2011 | Winterberg et al. |
| 7,968,758 | B2 | 6/2011 | Winterberg et al. |
| 7,977,523 | B2 | 7/2011 | Zanthoff et al. |
| 2003/0089279 | A1 | 5/2003 | Meyer et al. |
| 2006/0041167 | A1 | 2/2006 | Grass et al. |
| 2008/0058572 | A1 | 3/2008 | Fernandez et al. |
| 2009/0301345 | A1 * | 12/2009 | Mangold et al. ........... 106/31.13 |
| 2011/0118523 | A1 | 5/2011 | Winterberg et al. |
| 2011/0152596 | A1 | 6/2011 | Zanthoff et al. |
| 2011/0217552 | A1 | 9/2011 | Schulze-Isfort et al. |
| 2012/0142985 | A1 | 6/2012 | Winterberg et al. |
| 2012/0203047 | A1 | 8/2012 | Ryu |

FOREIGN PATENT DOCUMENTS

| | | |
|---|---|---|
| CN | 101486622 A | 7/2009 |
| EP | 0 995 718 | 4/2000 |
| EP | 1 266 864 | 12/2002 |

OTHER PUBLICATIONS

International Search Report Issued May 16, 2012 in PCT/EP12/51839 Filed Feb. 3, 2012.
U.S. Appl. No. 13/880,862, filed Jul. 3, 2013, Winterberg et al.
U.S. Appl. No. 14/005,479, filed Sep. 16, 2013, Winterberg et al.

* cited by examiner

*Primary Examiner* — Melvin C Mayes
*Assistant Examiner* — James Corno
(74) *Attorney, Agent, or Firm* — Oblon, McClelland, Maier & Neustadt, L.L.P.

(57) ABSTRACT

Silicon-aluminum mixed oxide powder having a weight ratio of $(Al_2O_3/SiO_2)_{tot}$ in the total primary particle of from 0.003 to 0.05, a weight ratio $(Al_2O_3/SiO_2)_{surface}$ of the primary particles in a surface layer having a thickness of about 5 nm which is less than in the total primary particle and a BET surface area of from 50 to 250 m$^2$/g. It is prepared by igniting one or more silicon compounds selected from the group consisting of $CH_3SiCl_3$, $(CH_3)_2SiCl_2$, $(CH_3)_3SiCl$ and $(n-C_3H_7)SiCl_3$, a hydrolysable and oxidizable aluminum compound, at least one fuel gas and air and burning the flame into a reaction chamber, subsequently separating the solid from gaseous materials and subsequently treating the solid with water vapor. The silicon-aluminum mixed oxide powder can be used as catalyst.

7 Claims, No Drawings

SILICON-ALUMINUM MIXED OXIDE POWDER

The invention relates to a silicon-aluminum mixed oxide powder, its preparation and use.

Isoolefins such as isobutene are important intermediates for the preparation of many organic compounds. In industrial streams, isoolefins are usually present together with other olefins and saturated hydrocarbons having the same number of carbon atoms. The isoolefins cannot be separated off economically from these mixtures using solely physical separation methods.

Isobutene is usually separated off from $C_4$ fractions, for example the $C_4$ fraction from a steam cracker, by, after removal of the major part of the multiply unsaturated hydrocarbons, mainly butadiene, converting the remaining mixture into linear butenes. When methanol is used, methyl tert-butyl ether (MTBE) is formed from isobutene, when ethanol is used, ethyl tert-butyl ether (ETBE) is formed and when water is used, tert-butanol (TBA) is formed. After having been separated off, these derivatives can be dissociated to form isobutene in a reversal of their formation. The dissociation of alkyl tert-butyl ethers (ATBE) into the corresponding isoolefins and alcohols and also the dissociation of tertiary alcohols into the corresponding isoolefins and water can be carried out in the presence of catalysts.

Many catalysts for the dissociation of alkyl tert-alkyl ethers (ATAE), in particular MTBE, and tertiary alcohols to the corresponding isoolefins and alcohol or water have been described. In U.S. Pat. No. 4,254,290, a 3:1 $SiO_2/Al_2O_3$ mixed oxide is used as catalyst.

EP-A-45159 discloses a silicon-aluminum mixed oxide powder for the dissociation of alkyl tert-alkyl ethers which has a proportion of 2-98% by weight of aluminum oxide and is obtained by milling and calcining coarser material. DE-A-2924869 describes a catalyst for the dissociation of alkyl tert-alkyl ethers which is based on a silicon-aluminum mixed oxide containing from 0.06 to 0.25% by weight of aluminum oxide. The mixed oxide is obtained by coprecipitation of tetraethyl orthosilicate and aluminum nitrate nonahydrate.

EP-A-589557 discloses a silicon-aluminum mixed oxide which contains an alkali metal oxide or alkaline earth metal oxide as further component. It is prepared by impregnating a silicon-aluminum mixed oxide prepared by precipitation with an aqueous solution of an alkali metal or alkaline earth metal salt.

EP-A-1894621 discloses a catalyst comprising from 0.5 to 20% by mass of alkali metal oxide and/or alkaline earth metal oxide, from 4 to 30% by mass of aluminum oxide and from 60 to 95% by mass of silicon dioxide. It is obtained by treating a silicon-aluminum mixed oxide prepared by precipitation with an aqueous alkali metal or alkaline earth metal salt solution under acidic conditions and subsequently calcining the product.

EP-A-23588 discloses a process for preparing a silicon-aluminum mixed oxide powder having a BET surface area of from 50 to 200 $m^2/g$ and a silicon dioxide content of from 0.5 to 20% by weight, in which gaseous aluminum chloride is introduced together with air into the mixing chamber of a burner, mixing it there with hydrogen and silicon tetrachloride and burning the mixture in a reaction chamber.

EP-A-585544 discloses a process for preparing a silicon-aluminum mixed oxide powder having a BET surface area of from 20 to 200 $m^2/g$ and a silicon dioxide content of from 15 to 35% by weight, in which gaseous silicon halides and aluminum halides together with a carrier gas are homogeneously mixed with air, oxygen and hydrogen in a mixing unit, the mixture is fed into a burner and reacted in a flame within a combustion chamber.

EP-A-850876 discloses a process for preparing doped silicon dioxide powders. Here, a gaseous silicon dioxide precursor and, as doping component, an aerosol of a metal salt solution are reacted in a flame. Due to the fine dispersion of the doping component in the aerosol, the doping medium is finely dispersed in the gas phase during formation of the oxide, so that the doping component is homogeneously incorporated into the oxide.

In EP-A-995718, this process is used for preparing a silicon dioxide powder doped with aluminum oxide. The powder prepared in this way is said to be able to be used as catalyst. However, it has been found that the dissociation of alkyl tert-butyl ethers (ATBE) into the corresponding isoolefins and alcohols and also the dissociation of tertiary alcohols into the corresponding isoolefins and water is not satisfactory when this is used.

The known catalysts have at least one of the following disadvantages in the dissociation of ATBE or tertiary alcohols into isoolefin and alcohol or water:
i. formation of undesirable by-products such as dimethyl ether or oligomers of the product olefins
ii. short operating life of the catalyst
iii. increased formation of by-products when the reaction temperature is raised to compensate for a decrease in activity
iv. complicated and thus costly preparation of the catalyst.

It was therefore a technical object of the invention to provide a catalyst by means of which the abovementioned disadvantages can be minimized or entirely avoided.

It has now surprisingly been found that the technical object is achieved by a silicon-aluminum mixed oxide powder which is present predominantly or entirely in the form of aggregated primary particles and in which
a. the weight ratio of $(Al_2O_3/SiO_2)_{ttl}$ in the total primary particle is from 0.002 to 0.05, preferably from 0.003 to 0.015, particularly preferably from 0.005 to 0.01,
b. the weight ratio $(Al_2O_3/SiO_2)_{surface}$ of the primary particles in a surface layer having a thickness of about 5 nm is less than in the total primary particle and
c. the BET surface area is from 50 to 250 $m^2/g$, preferably from 100 to 200 $m^2/g$.

In the silicon-aluminum mixed oxide powder of the invention, the proportion of aluminum oxide is very low compared to the silicon dioxide and the weight ratio $(Al_2O_3/SiO_2)_{surface}$ of the primary particles in a surface layer is less than in the total primary particle. This means that the aluminum oxide concentration at the surface is reduced further. The total primary particle includes the proportion of silicon dioxide and aluminum oxide in the surface layer. Preference can be given to a silicon-aluminum mixed oxide powder according to the invention in which $(Al_2O_3/SiO_2)_{ttl}/(Al_2O_3/SiO_2)_{surface}$ is from 1.3 to 20, preferably from 1.4 to 10 and particularly preferably from 1.6 to 5, where "ttl." denotes the total primary particle.

In a preferred embodiment of the invention, the silicon-aluminum mixed oxide powder has a weight ratio of $(Al_2O_3/SiO_2)_{ttl}$ of from 0.005 to 0.015, a ratio of $(Al_2O_3/SiO_2)_{ttl}/(Al_2O_3/SiO_2)_{surface}$ of from 1.3 to 20 and a BET surface area of from 100 to 200 $m^2/g$.

It is therefore surprising that the silicon-aluminum mixed oxide powder of the invention displays both a comparable catalytic activity and a lower formation of undesirable by-products in, for example, the gas-phase dissociation of methyl tert-butyl ether or of tert-butyl alcohol compared to the processes of the prior art.

For the purposes of the present invention, a mixed oxide powder is an intimate mixture of the mixed oxide components aluminum oxide and silicon dioxide at an atomic level, in which the primary particles also have Si—O—Al bonds. The surfaces of these primary particles are largely or completely free of pores. Preference can be given to silicon-aluminum mixed oxide powders according to the invention which have been obtained by flame hydrolysis and/or flame oxidation of silicon compounds and aluminum compounds in a flame generated by the reaction of hydrogen and oxygen. These powders are described as "pyrogenic" or "fumed". The reaction initially forms finely divided primary particles which during the further course of the reaction grow together to form aggregates and the latter can associate further to form agglomerates.

The weight ratio on the surface can be determined, for example, by X-ray-induced photoelectron spectroscopy (XPS analysis) of the powder. Additional information on the surface composition can be obtained by energy-dispersive X-ray analysis (TEM-EDX analysis) of individual primary particles.

The weight ratio in the total primary particle is determined by chemical or physicochemical methods, e.g. X-ray fluorescence analysis of the powder.

Furthermore, it has been found that it can be advantageous for the silicon-aluminum mixed oxide powder to have a dibutyl phthalate number, in g of dibutyl phthalate (DBP)/100 g of mixed oxide, of from 300 to 350. The DBP number is a measure of the structure of aggregates. Low numbers correspond to a low-level structure, while high numbers correspond to a high-level structure. The preferred range from 300 to 350 corresponds to a high-level structure. In DBP absorption, the force taken up, for example the torque (in Nm), by the rotating blades of the DBP measurement instrument on addition of defined amounts of DBP, comparable to a titration, is measured. Here, the powder according to the invention displays a sharply pronounced maximum with a subsequent decrease at a particular addition of DBP. The dibutyl phthalate absorption can be measured, for example, using a RHEOCORD 90 instrument from Haake, Karlsruhe. For this purpose, 12 g of the silicon-aluminum mixed oxide powder are weighed out to within 0.001 g and introduced into a kneading chamber, the latter is closed by means of a lid and dibutyl phthalate is metered in through a hole in the lid at a predetermined metering rate of 0.0667 ml/s. The kneader is operated at a motor speed of 125 revolutions per minute. After the torque maximum has been reached, the kneader and the introduction of DBP are automatically switched off. The DBP absorption is calculated from the amount of DBP consumed and the amount of particles weighed in according to: DBP number (g/100 g)=(consumption of DBP in g/weight of powder in g)×100.

The invention further provides a process for preparing the silicon-aluminum mixed oxide powder of the invention, in which a) a vapor containing one or more silicon compounds selected from the group consisting of $CH_3SiCl_3$, $(CH_3)_2SiCl_2$, $(CH_3)_3SiCl$ and $(n-C_3H_7)SiCl_3$ and the vapor of a hydrolysable and oxidizable aluminum compound are introduced separately or together by means of a carrier gas into a mixing chamber, where the weight ratio of aluminum compound, calculated as $Al_2O_3$, to silicon compound, calculated as $SiO_2$, is from 0.003 to 0.05, b) separately therefrom, at least one fuel gas and air are introduced into this mixing chamber, where the total amount of oxygen in the air is at least sufficient for complete combustion of the fuel gas and the silicon compounds and aluminum compounds, c) the mixture of the vapor of the silicon compounds and the aluminum compounds, fuel gas and air is ignited in a burner and the flame burns into a reaction chamber, d) the solid is subsequently separated from gaseous materials and the solid is subsequently treated with water vapor.

The process can also be carried out with the vapor of the silicon compounds containing up to 40% by weight of $SiCl_4$. A mixture of from 65 to 80% by weight of $CH_3SiCl_3$ and from 20 to 35% by weight of $SiCl_4$ can be particularly preferred. As aluminum compound, preference is given to aluminum chloride. The fuel gas is preferably selected from the group consisting of hydrogen, methane, ethane, propane and mixtures thereof. Particular preference is given to hydrogen. The air introduced into the mixing chamber is at least sufficient for complete combustion of the fuel gas and the silicon compounds and aluminum compounds. In general, an excess of air is used. The treatment with water vapor serves to at least largely remove chloride residues adhering to the particles so that the powder contains not more than 1% by weight of chloride, preferably not more than 0.2% by weight of chloride.

The invention further provides for the use of the silicon-aluminum mixed oxide powder as catalyst.

EXAMPLES

Example 1

Preparation of the Silicon-Aluminum Mixed Oxide Powder of the Invention

The vapor of a mixture consisting of 45 kg/h of $CH_3SiCl_3$ and 15 kg/h of $SiCl_4$ and the vapor of 0.6 kg/h of aluminum chloride are introduced separately from one another by means of nitrogen as carrier gas into a mixing chamber. The vapors are mixed with 14.6 standard m³/h of hydrogen and 129 standard m³/h of dried air in the mixing chamber of a burner, fed via a central tube, at the end of which the reaction mixture is ignited, into a water-cooled flame tube and burnt there. The powder formed is subsequently deposited in a filter and treated with water vapor at 400-700° C. The powder contains 99% by weight of silicon dioxide and 1% by weight of aluminum oxide. The BET surface area is 173 m²/g. The DBP number is 326 g/100 g of mixed oxide.

To determine the weight ratio $(Al_2O_3/SiO_2)_{surface}$ of the primary particles in a surface layer having a thickness of about 5 nm, XPS analysis is employed. This gives a weight ratio $(Al_2O_3/SiO_2)_{surface}$ of 0.0042. The determination of the weight ratio $(Al_2O_3/SiO_2)_{ttl}$ in the total primary particle is carried out by X-ray fluorescence analysis on the powder. It gives a weight ratio $(Al_2O_3/SiO_2)_{ttl}$ of 0.010. This gives a value for $(Al_2O_3/SiO_2)_{ttl}/(Al_2O_3/SiO_2)_{surface}$ of 2.4.

Example 2

Comparative Example

Silicon-aluminum mixed oxide powder having a $Al_2O_3$ content of 0.27% by weight disclosed in EP-A-995718, Example 2, serves as comparative material. It is prepared in a process disclosed in EP-A-850876, which makes it possible to distribute the aluminum oxide content homogeneously. The powder has a BET surface area of 204 m²/g.

Example 3

Comparative Example 24.5 standard m³/h of hydrogen are mixed with 129 standard m³/h of air and 80 kg/h of SiCl₄ vapor, 8.1 kg/h of AlCl₃ vapor are subsequently added and the reaction mixture is burnt in a flame tube into which 80 standard m³/h of air are additionally added. After passing the flame tube, the powder formed is separated off from gaseous materials in a filter and adhering hydrochloric acid residues are removed by treatment with water vapor.

The powder has a proportion of aluminum oxide of 9.3% by weight. The BET surface area is 195 m²/g.

Example 4

Gas-phase dissociation of methyl tert-butyl ether (MTBE)

The powders from Examples 1 to 3 are mixed in a ratio of 1:5 with granulated quartz. Specialyst 071, Evonik Degussa GmbH, an aluminosilicate having an aluminum content of 21% by mass (calculated as $Al_2O_3$) and doped with 10% by mass of magnesium (calculated as MgO) is used as reference material. The specific velocity over the catalyst (WHSV; gram of feed per gram of catalyst per hour) is varied in the range from 5 to 50 h⁻¹.

Table 1 shows the results of the MTBE dissociation using the powder according to the invention from Example 1 compared to the powders which are not according to the invention from Examples 2 and 3 and also the reference material, viz. commercial catalyst Specialyst 071 (likewise as powder).

TABLE 1

| | Dissociation of MTBE | | | |
|---|---|---|---|---|
| Powder | WHSV h⁻¹ | MTBE conversion % | DME selectivity % | C₈ selectivity % |
| Example 1 | 18 | 85 | 0.63 | 0.06 |
| Example 2 | 25 | 85 | 1.49 | 0.17 |
| Example 3 | 18 | 85 | 1.16 | 0.03 |
| Specialyst 071 | 8 | 85 | 2.29 | 0.10 |

Reaction conditions: 225° C., 6 bar gauge, 0.2 g of catalyst; results were obtained after 100 h on stream.

It can be seen that the reference material with a DME selectivity of 2.29% has the highest value of all powders tested. The catalytic activity is likewise relatively low since a low WHSV of 8 h⁻¹ has to be set in order to achieve the conversion of 85%. The C₈ selectivity is likewise quite high at 0.1%.

In comparison, the powder according to the invention from Example 1 displays the best results. The conversion of 85% is achieved at an WHSV as low as 18 h⁻¹. At the same time, the selectivities to DME and C₈ are very low with values of 0.63% and 0.06%, respectively.

The powder from Example 2 displays even lower selectivities to the by-products, but owing to its low catalytic activity gives a conversion of only 35% at an WHSV of 8 h⁻¹.

The powder from Example 3 displays a poorer DME selectivity, viz. 1.16%, than the powder according to the invention from Example 1.

The invention claimed is:

1. A silicon-aluminum mixed oxide powder, wherein:
   the silicon-aluminum mixed oxide powder includes aggregated primary particles,
   a weight ratio $(Al_2O_3/SiO_2)_{ttl}$ in total primary particles is from 0.003 to 0.05,
   a weight ratio $(Al_2O_3/SiO_2)_{surface}$ of primary particles in a surface layer having a thickness of about 5 nm is less than the weight ratio $(Al_2O_3/SiO_2)_{ttl}$ in the total primary particles, and
   a BET surface area is from 50 to 250 m²/g.

2. The silicon-aluminum mixed oxide powder of claim 1, wherein
   $(Al_2O_3/SiO_2)_{ttl}/(Al_2O_3/SiO_2)_{surface}$ is from 1.3 to 20.

3. The silicon-aluminum mixed oxide powder of claim 2, wherein
   a dibutyl phthalate number, measured in g of dibutyl phthalate per 100 g of the silicon-aluminum mixed oxide powder, is from 300 to 350.

4. The silicon-aluminum mixed oxide powder of claim 1, wherein
   a dibutyl phthalate number, measured in g of dibutyl phthalate per 100 g of the silicon-aluminum mixed oxide powder, is from 300 to 350.

5. A process for preparing the silicon-aluminum mixed oxide powder of claim 1,
   the process comprising:
   (i) introducing, either separately or together, via a carrier gas into a mixing chamber, a vapor comprising one or more silicon compounds selected from the group consisting of $CH_3SiCl_3$, $(CH_3)_2SiCl_2$, $(CH_3)_3SiCl$ and $(n-C_3H_7)SiCl_3$, and a vapor comprising a hydrolysable, oxidizable, or both hydrolysable and oxidizable aluminum compound wherein a weight ratio of the aluminum compound, calculated as $Al_2O_3$, to the silicon compounds, calculated as $SiO_2$, is from 0.003 to 0.05,
   (ii) introducing, separately, at least one fuel gas and air into the mixing chamber, wherein a total amount of oxygen in the air is at least sufficient for complete combustion of the at least one fuel gas, the silicon compounds and the aluminum compound,
   (iii) igniting a mixture of the vapor comprising the silicon compounds, the vapor comprising the aluminum compound, the at least one fuel gas, and the air in a burner to obtain a flame, and burning the flame into a reaction chamber, and
   (iv) subsequently separating solid from gaseous materials, and subsequently treating the solid with water vapor, thereby obtaining the silicon-aluminum mixed oxide powder.

6. The process of claim 5, wherein
   the vapor comprising the silicon compounds comprises up to 40% by weight of $SiCl_4$.

7. A catalyst, comprising the silicon-aluminum mixed oxide powder of claim 1.

* * * * *